(12) United States Patent
Skurkovich et al.

(10) Patent No.: US 7,462,454 B2
(45) Date of Patent: Dec. 9, 2008

(54) TREATMENT OF HERPES

(75) Inventors: Boris Skurkovich, Pawtucket, RI (US); Simon Skurkovich, Rockville, MD (US)

(73) Assignee: Advanced Biotherapy, Inc., Woodland Hills, CA (US)

( * ) Notice: Subject to any disclaimer, the term of this patent is extended or adjusted under 35 U.S.C. 154(b) by 48 days.

(21) Appl. No.: 11/245,701

(22) Filed: Oct. 7, 2005

(65) Prior Publication Data

US 2006/0194221 A1     Aug. 31, 2006

Related U.S. Application Data

(60) Provisional application No. 60/643,572, filed on Jan. 13, 2005, provisional application No. 60/617,770, filed on Oct. 12, 2004.

(51) Int. Cl.
*C12Q 1/68* (2006.01)

(52) U.S. Cl. ............................................. 435/6; 435/7.1

(58) Field of Classification Search ..................... 435/6, 435/7.1

See application file for complete search history.

(56) References Cited

U.S. PATENT DOCUMENTS

| | | | |
|---|---|---|---|
| 4,704,362 A | 11/1987 | Itakura et al. |
| 4,897,264 A | 1/1990 | Novick et al. |
| 4,968,607 A | 11/1990 | Dower |
| 5,126,262 A | 6/1992 | Matsui et al. |
| 5,221,789 A | 6/1993 | Novick et al. |
| 5,578,707 A | 11/1996 | Novick |
| 5,626,843 A | 5/1997 | Skurkovich et al. |
| 5,759,808 A | 6/1998 | Casterman et al. |
| 5,800,988 A | 9/1998 | Casterman et al. |
| 5,840,526 A | 11/1998 | Casterman et al. |
| 5,888,511 A | 3/1999 | Skurkovich et al. |
| 6,015,695 A | 1/2000 | Casterman et al. |
| 6,180,370 B1 | 1/2001 | Queen et al. |

FOREIGN PATENT DOCUMENTS

WO     87/02671     5/1987

OTHER PUBLICATIONS

Bird et al., "Single-Chain Antigen-Binding Proteins," *Science*, vol. 242, pp. 423-426, 1988.

Engleman et al., "Antibodies to a Soluble Form of a Tumor Necrosis Factor (TNF) Receptors Have TNF-Like Activity," *The Journal of Biological Chemistry*, vol. 265, No. 24, pp. 14497-14504, 1990.

Feldmann et al., "Interferons and Autoimmunity," *Interferon 9*, Academic Press, pp. 75-89, 1987.

Fountoulakis et al., "Purification and Biochemical Characterization of a Soluble Human Interferon γ Receptor Expressed in *Escherichia coli*," *J. Biol. Chem.*, vol. 265, pp. 13268-13275, 1990.

Fountoulakis et al., "Interferon γ Receptor Extracellular domain Expressed as IgG Fusion Protein in Chinese Hamster Ovary Cells," *The Journal of Biological Chemistry*, vol. 270, pp. 3958-3964, 1995.

Gillam et al., "Site-Specific Mutagenesis Using Synthetic Oligodeoxyribonucleotide Primers: I. Optimum Conditions and Minimum Oligodeoxyribonucleotide Length," *Gene*, vol. 8, pp. 81-97, 1979.

Gray et al., "Cloning of Human Tumor Necrosis Factor (TNF) Receptor cDNA and Expression of Recombinant Soluble TNF-binding Protein," *Proc. Natl. Acad. Sci. USA*, vol. 87, pp. 7380-7384, 1990.

Gringeri et al., "Anti-Alpha Interferon Immunization: Safety and Immunogenicity in Asymptomatic HIV Positive Patients at High Risk of Disease Progression," *Cellular and Molecular Biology*, vol. 41, pp. 381-387, 1995.

Gringeri et al., "Absence of Clinical, Virological, and Immunological Signs of Progression in HIV-1 Infected Patients Receiving Active Anti-Interferon-α Immunization: A 30-month Follow-up Report," *Journal of Acquired Immune Deficiency Syndromes and Human Retrovirology*, vol. 13, pp. 55-67, 1996.

Gu et al., "Construction and Expression of Mouse-Human Chimeric Antibody SZ-51 Specific for Activated Platelet P-Selectin," *Thrombosis and Hematocyst*, vol. 77, pp. 755-759, 1997.

Hamers-Casterman et al., "Naturally Occurring Antibodies Devoid of Light Chains," *Letters to Nature*, vol. 363, pp. 446-448, 1993.

Huston, et al., "Protein Engineering of Antibody Binding Sites: Recovery of Specific Activity in an Anti-Digoxin Single-Chain Fv Analogue Produced in *Escherichia coli*," *Proc. Natl. Acad. Sci., USA*, vol. 85, pp. 5879-5883, 1988.

Matsuda et al., "Establishment of an Interleukin 6 (IL 6) Cell Stimulatory Factor 2-Dependent Cell Line and Preparation of Anti-IL 6 Monoclonal Antibodies," *Eur. J. Immunol.*, vol. 18, pp. 951-956, 1988.

Mesa et al., "Interferon-γ Receptor Extracellular Domain-IgG Fusion Protein Produced in Chinese Hamster Ovary Cells as Mixture of Glycoforms," *Journal Of Interferon and Cytokine Research*, vol. 15, pp. 309-315, 1995.

(Continued)

*Primary Examiner*—Ali R. Salimi

(74) *Attorney, Agent, or Firm*—Drinker Biddle & Reath, LLP

(57) ABSTRACT

The present invention includes methods for the treatment of a herpes simplex virus infection comprising the administration of inhibitors of gamma interferon, tumor necrosis alpha and interleukin-1.

8 Claims, No Drawings

OTHER PUBLICATIONS

Ohshima et al., "Polyclonal Antibody Against an Inducible Form of Nitric Oxide Synthase Purified from the Liver of Rats Treated with Propionibacterium Acnes and Lipopolysaccharide," vol. 187, pp. 1291-1297, 1992.

Peppel et al., "A Tumor Necrosis Factor (TNF) Receptor-IgG Heavy Chain Chimeric Protein as a Bivalent Antagonist of TNF Activity," *J. Exp. Med.* vol. 174, pp. 1483-1489, 1991.

Queen et al., "Cell-Type Specific Regulation of a κ Immunoglobulin Gene by Promoter and Enhancer Elements." *Immunol. Rev.*, vol. 89, pp. 49-68, 1986.

Roberts et al., "Generation of an Antibody With Enhanced Affinity and Specificity for its Antigen by Protein Engineering," *Nature*, vol. 328, pp. 731-734, 1987.

Sastry et al., "Cloning of the Immunological Repertoire in *Escherichia coli* for Generation of Monoclonal Catalytic Antibodies: Construction of a Heavy Chain Variable Region-Specific cDNA Library," *Proc. Nat'l. Acad. Sci. USA*, vol. 86, pp. 5728-5732, 1989.

Schall et al., "Molecular Cloning and Expression of a Receptor for Human Tumor Necrosis Factor," *Cell*, vol. 61, pp. 361-370, 1990.

Seligmann et al., "Heavy Chain Diseases: Current findings and Concepts," *Immunological Rev.* vol. 48, pp. 145-167, 1979.

Singh et al., Dysregulated Expression of IFN-γ and IL-10 and impaired IFN-γ Mediated Responses at Different Disease Stages in Patients with Genital Herpes Simplex Virus-2 Infection, *Clin. Exp. Immunol.*, vol. 133, pp. 97-107, 2003.

Skurkovich et al., "Immunosuppressive Effect of an Anti-interferon Serum," *Nature*, vol. 247, pp. 551-552, Feb. 22, 1974.

Skurkovich et al., "The Probable Role of Interferon in Allergy," *Annals of Allergy*, vol. 35, pp. 356-360, Dec. 1975.

Skurkovich et al., "Aberrant IFN May Help HIV Survive and Replicate; Its Removal in AIDS Patients May Halt This Process and Help Restore the Immune System," *Journal of IFN Research*, vol. 12, Suppl. 1, p. S110, 1992.

Skurkovich et al., "A Disturbance of Interferon Synthesis With the Hyperproduction of Unusual Kinds of Interferon can Trigger Autoimmune Disease and Play a Pathogenetic Role in AIDS: The Removal of These Interferons can be Therapeutic," *Medical Hypotheses*, vol. 41, pp. 177-185, 1993.

Skurkovich et al., "A Disturbance of Interferon Synthesis With the Hyperproduction of Unusual Kinds of Interferon can Trigger Autoimmune Disease and Play a Pathogenetic Role in AIDS: The Removal of These Interferons can be Therapeutic," *Medical Hypotheses*, vol. 42, pp. 27-35, 1994.

Tuszynski et al., "Thrombospondin Promotes Platelet Aggregation," *Blood*, vol. 72, pp. 109-115, 1988.

Ward et al. "Binding Activities of a Repertoire of Single Immunoglobulin Variable Domains Secreted From *Escherichia coli*," *Nature*, vol. 341, pp. 544-546, 1989.

Wright et al., "Genetically Engineered Antibodies: Progress and Prospects," *Critical Rev. in Immunol.* vol. 12, pp. 125-168, 1992.

Zagury et al., Toward a New Generation of Vaccines: The Anti-Cytokine Therapeutic Vaccines, *Proc. Nat'l. Acad. Sci., USA*, vol. 98(14), pp. 8024-8029, 2001.

TREATMENT OF HERPES

CROSS-REFERENCE TO RELATED APPLICATIONS

The present application is entitled to priority under 35 U.S.C § 119(e), to U.S. Provisional Application No. 60/617,770, filed Oct. 12, 2004 and U.S. Provisional Application No. 60/643,572, filed Jan. 13, 2005, all of which are incorporated by reference in their entirety herein.

BACKGROUND OF THE INVENTION

The ability of the mammalian immune system to recognize "self" versus "non-self" antigens is vital to successful host defense against invading microorganisms. "Self" antigens are those which are not detectably different from an animal's own constituents, whereas "non-self" antigens are those which are detectably different from or foreign to the mammal's constituents. A normal mammalian immune system functions to recognize "non-self antigens" and attack and destroy them. An autoimmune disorder such as for example, rheumatoid arthritis, insulin-independent diabetes mellitus, acquired immune deficiency syndrome (AIDS), multiple sclerosis, and the like, results when the immune system identifies "self" antigens as "non-self", thereby initiating an immune response against the mammal's own body components (i.e., organs and/or tissues). This creates damage to the mammal's organs and/or tissues and can result in serious illness or death.

Predisposition of a mammal to an autoimmune disease is largely genetic; however, exogenous factors such as viruses, bacteria, or chemical agents may also play a role. Autoimmunity can also surface in tissues that are not normally exposed to lymphocytes such as for example, neural tissue. When a tissue not normally exposed to lymphocytes becomes exposed to these cells, the lymphocytes may recognize the surface antigens of these tissues as "non-self" and an immune response may ensue. Autoimmunity may also develop as a result of the introduction into the animal of antigens which are sensitive to the host's self antigens. An antigen which is similar to or cross-reactive with an antigen in an mammal's own tissue may cause lymphocytes to recognize and destroy both "self" and "non-self" antigens.

It has been suggested that the pathogenesis of autoimmune diseases is associated with a disruption in synthesis of interferons and other cytokines often induced by interferons (Skurkovich et al., Nature 217:551-552, 1974; Skurkovich et al., Annals of Allergy, 35:356, 1975; Skurkovich et al., J. Interferon Res. 12, Suppl. 1:S110, 1992; Skurkovich et al., Med. Hypoth., 41:177-185, 1993; Skurkovich et al., Med. Hypoth., 42:27-35, 1994; Gringeri et al., Cell. Mol. Biol. 41(3):381-387, 1995; Gringeri et al., J. Acquir. Immun. Defic. Syndr., 13:55-67, 1996). Cytokines are substances produced in different cell territories, including immune and nerve cells, which communicate with and affect the action of cells. In particular, gamma interferon plays a significant pathogenic role in autoimmune dysfunction. Gamma interferon stimulates cells to produce elevated levels of HLA class II antigens (Feldman et al., 1987, "Interferons and Autoimmunity", In: IFN (, p. 75, Academic Press). It is known that gamma interferon participates in the production of tumor necrosis factor (TNF), and it is also known that TNF also plays a role in stimulation of production of autoantibodies. In view of this, therapies to modulate these cytokines have been developed. Clinical success in treating several autoimmune diseases using antibodies to gamma interferon has been reported (Skurkovich et al., U.S. Pat. No. 5,888,511).

Viral diseases pathogeneses may develop not by the virus itself but from the interferon induced by the presence of the virus in infected cells and tissues. In these cases, interferon acts mostly as a pathological agent which, together with the viruses which induce interferon, exerts a pathological effect on the organism. The AIDS virus, rubella virus, herpes simplex virus 2, herpes simplex type 1, varicella, and certain other viruses and bacteria which participate in psychiatric and neurological disorders, and some chemical agents, could be considered as responsible for the induction of pathological interferon in infected patients. It is therefore possible that interferon, especially gamma interferon, can contribute to the pathology of these diseases.

The hyperproduction of gamma interferon induced by viruses and the like can also disturb the production of normal interferon. A critical step in the treatment of patients with disturbances in the production of gamma interferon can be the removal or destruction of this abnormal interferon induced by these agents. If not removed, the abnormal interferon brings on a vicious cycle of continued immune dysregulation and tissue injury. The dysregulated production of gamma interferon at different stages during genital herpes and the impaired ability of monocytic cells to respond to gamma interferon has been suggested as playing a role in the pathogenesis of recurrent genital herpes disease (Singh et al., 2003, Clin. Exp. Immunol., 133: 97-107). Further, because the production of gamma interferon is associated with interleukin-1 (IL-1) and tumor necrosis factor-alpha (TNF alpha), these cytokines may also participate in the pathological action.

Herpes is an infection caused by the herpes simplex virus (HSV). There are two types of HSV, and both can cause genital herpes. HSV type 1 most commonly infects the lips, causing sores known as fever blisters or cold sores, but it also can infect the genital area and produce sores. HSV type 2 is the usual cause of genital herpes, but it also can infect the mouth. Both HSV 1 and 2 can produce sores (also called lesions) in and around the vaginal area, on the penis, around the anal opening, and on the buttocks or thighs. Occasionally, sores also appear on other parts of the body where the virus has entered through broken skin. HSV remains in certain nerve cells of the body for life, and can produce symptoms off and on in some infected people.

Cold sores are usually caused by (HSV-1). The HSV-1 virus is part of the same virus family that causes chickenpox (varicella-zoster), shingles (herpes zoster), and genital herpes (herpes simplex virus type 2). HSV-1 infections are extremely common because the virus is very contagious and can spread through physical contact, such as kissing. Once a patient is infected with HSV-1 the virus localizes to neurons and remains either dormant or activated for the rest of the patient's life.

Common activators of HSV-1, and HSV-2 include; stress, fatigue, a cold, fever, influenza, exposure to the sun or other forms of UV rays, cold weather, hormonal changes, such as those associated with menstruation or pregnancy, and trauma at the site of the cold sore, such as shaving cuts or dental work.

Herpes lesions outbreaks generally last for 7-10 days and occur about three to four times a year. Further, herpes cold sores tend to occur in the following stages. The virus is activated from its dormancy in neurons and travels through nerve endings towards the skin, including the lips and genitals. This is usually accompanied by a tingling, itching, or burning sensation beneath the surface of the skin, usually around the site where lesions will appear. This stage of a herpes infection is known as the prodrome stage. About a day after this stage, small red bumps appear in a group, which begin to blister into a herpes lesion. After a number of days, usually about 3-4, the blisters dry up and form a yellow crust. The crust eventually falls off, leaving a red tender area. The redness subsequently fades as the immune system recognizes and attacks the herpes virus, the virus retreats to the immune privileged sites of the nervous system, and the redness fades.

Recent estimates have determined that in 45 million people in the United States ages 12 and older, approximately one out of every five members of the total adolescent and adult population, are infected with HSV-2. Further, HSV-2 accounts for approximately 90-95% of genital herpes cases and can be transmitted through oral or genital secretions.

There is no cure for herpes, either HSV-1 or HSV-2. However, three prescription drugs are available for treating herpes, especially genital herpes, as well as preventing future outbreaks. These drugs include, Acyclovir (Zovirax™), Famciclovir (Famvir™) and Valacyclovir (Valtrex™). In addition, Valacyclovir is indicated for treating cold sores. However, it is often recommended that these medications be administered at the first signs of a herpes cold sore, and their efficacy during the advanced stages of a herpes cold sore outbreak are less well known.

There exists a need for a method of treating a herpes simplex virus infection and the immune dysregulation associated with such infections. The present invention provides such methods and compositions.

SUMMARY OF THE INVENTION

The present invention includes a method of treating a herpes simplex virus infection in a patient comprising administering to the patient an effective amount of an antibody to gamma interferon.

In one aspect of the present invention, the antibody is selected from the group consisting of a polyclonal antibody, a monoclonal antibody, a humanized antibody, a synthetic antibody, a heavy chain antibody, a biologically active fragment of an antibody, wherein the biologically active fragment is a Fab fragment, a F(ab')$_2$ fragment, a Fv fragment, and combinations thereof.

In another aspect of the invention, the antibody is administered by the route selected from the group consisting of intramuscularly, intravenously, intradermally, cutaneously, ionophoretically, topically, locally, and inhalation.

In still another aspect of the invention, the antibody is administered topically.

In yet another aspect of the invention, the antibody is selected from the group consisting of a polyclonal antibody, a monoclonal antibody, a synthetic antibody, a heavy chain antibody, a humanized antibody, a biologically active fragment of an antibody, wherein the biologically active fragment is a Fab fragment, a F(ab')$_2$ fragment, a Fv fragment, and combinations thereof.

In another aspect of the invention, the heavy chain antibody is selected from the group consisting of a camelid antibody, a heavy chain disease antibody, and a variable heavy chain immunoglobulin.

In yet another aspect of the invention, the herpes simplex virus infection is a herpes simplex type 1 infection.

In still another aspect of the invention, the herpes simplex virus infection is a herpes simplex type 2 infection.

The present invention includes a method of treating a herpes simplex virus infection in a patient, the method comprising administering to the patient a combination of an effective amount of an antibody to tumor necrosis factor alpha and an antibody to gamma interferon.

In one aspect of the present invention, the antibody is selected from the group consisting of a polyclonal antibody, a monoclonal antibody, a humanized antibody, a synthetic antibody, a heavy chain antibody, a biologically active fragment of an antibody, wherein the biologically active fragment is a Fab fragment, a F(ab')$_2$ fragment, a Fv fragment, and combinations thereof.

In another aspect of the invention, the antibody is administered by the route selected from the group consisting of intramuscularly, intravenously, intradermally, cutaneously, ionophoretically, topically, locally, and inhalation.

In still another aspect of the invention, the antibody is administered topically.

In one aspect of the present invention, the antibody is selected from the group consisting of a polyclonal antibody, a monoclonal antibody, a synthetic antibody, a heavy chain antibody, a humanized antibody, a biologically active fragment of an antibody, wherein the biologically active fragment is a Fab fragment, a F(ab')$_2$ fragment, a Fv fragment, and combinations thereof.

In another aspect of the invention, the heavy chain antibody is selected from the group consisting of a camelid antibody, a heavy chain disease antibody, and a variable heavy chain immunoglobulin.

In still another aspect of the invention, the herpes simplex virus infection is a herpes simplex type 1 infection.

In one aspect of the present invention, the herpes simplex virus infection is a herpes simplex type 2 infection.

The present invention includes a method of treating a herpes simplex virus infection in a patient, the method comprising administering to the patient a combination of an effective amount of an antibody to tumor necrosis factor alpha, an antibody to interleukin-1 and an antibody to gamma interferon.

In another aspect of the invention, the antibody is selected from the group consisting of a polyclonal antibody, a monoclonal antibody, a humanized antibody, a synthetic antibody, a heavy chain antibody, a biologically active fragment of an antibody, wherein the biologically active fragment is a Fab fragment, a F(ab')$_2$ fragment, a Fv fragment, and combinations thereof.

In one aspect of the present invention, the antibody is administered by the route selected from the group consisting of intramuscularly, intravenously, intradermally, cutaneously, ionophoretically, topically, locally, and inhalation.

In another aspect of the invention, the antibody is administered topically.

In still another aspect of the invention, the antibody is selected from the group consisting of a polyclonal antibody, a monoclonal antibody, a synthetic antibody, a heavy chain antibody, a humanized antibody, a biologically active fragment of an antibody, wherein the biologically active fragment is a Fab fragment, a F(ab')$_2$ fragment, a Fv fragment, and combinations thereof.

In another aspect of the invention, the heavy chain antibody is selected from the group consisting of a camelid antibody, a heavy chain disease antibody, and a variable heavy chain immunoglobulin.

In one aspect of the present invention, the herpes simplex virus infection is a herpes simplex type 1 infection.

In another aspect of the invention, the herpes simplex virus infection is a herpes simplex type 2 infection.

The present invention includes a kit for treating a herpes simplex virus infection in a patient, said kit comprising an antibody to gamma interferon and an antibody to tumor necrosis factor alpha and a pharmaceutically acceptable carrier, said kit further comprising an applicator, and an instructional material for the use thereof.

The present invention includes a kit for treating a herpes simplex virus infection in a patient, said kit comprising an antibody to gamma interferon and an antibody to tumor necrosis factor alpha and a pharmaceutically acceptable carrier, said kit further comprising an applicator, and an instructional material for the use thereof.

The present invention includes a kit for treating a herpes simplex virus infection in a patient, said kit comprising an antibody to gamma interferon, an antibody to interleukin-1 and an antibody to tumor necrosis factor alpha and a pharmaceutically acceptable carrier, said kit further comprising an applicator, and an instructional material for the use thereof.

DETAILED DESCRIPTION OF THE INVENTION

The present invention includes the discovery that administration of antibodies to gamma interferon, antibodies to TNF-alpha, and antibodies to IL-1, alone or in combination, to a patient with a herpes simplex virus infection, including both HSV-1 and HSV-2 infections, results in a decrease in the burning and the pain associated with a herpes simplex virus infection, and a increased time to healing of the infection. Herpes-family virus skin lesions can include those associated with HSV-1, HSV-2, herpes zoster virus, as well as other viruses of the herpes virus family. Further, other non-herpes viruses, such as non-oncogenic papilloma viruses, can cause skin lesions, such as warts.

As disclosed herein, antibodies to gamma interferon, antibodies to TNF-alpha and antibodies to IL-1, alone or in combination, are useful for the treatment of a herpes simplex virus infection. However, the invention should not be construed as being limited solely to the examples provided herein, as other viral mediated skin diseases which are at present unknown, once known, may also be treatable using the methods of the invention.

The invention includes a method of treating a herpes simplex virus infection, including a herpes simplex type 1 infection and a herpes simplex type 2 infection, in a patient. The method comprises administering to a patient with a herpes simplex virus infection, such as HSV-1 cold sores or HSV-2 genital herpes, an antibody to gamma interferon, an antibody to TNF-alpha and an antibody to IL-1, alone or in combination. The antibody can be administered using techniques well known in the art and disclosed elsewhere herein, including parenteral administration, such as intramuscular, intravenous, intradermal, cutaneous, subcutaneous or local administration. In addition, an antibody can be administered ionophoretically, topically, and via inhalation. Preferably, the antibody or combination of antibodies is administered, alone or in combination, to the skin topically. The method can be used to treat an autoimmune or inflammatory skin disease in any mammal; however, preferably, the mammal is a human.

The antibodies to gamma interferon useful in the methods of the invention may be polyclonal antibodies, monoclonal antibodies, synthetic antibodies, such as a biologically active fragment of an antibody to gamma interferon, or they may be humanized monoclonal antibodies. Methods of making and using each of the types of antibodies useful in the methods of the invention are now described. In addition, human antibodies to gamma interferon, TNF-alpha or IL-1, obtained from human donors, may be employed in the invention.

When the antibody used in the methods of the invention is a polyclonal antibody (IgG), the antibody is generated by inoculating a suitable animal with gamma interferon, TNF-alpha, IL-1, or a fragment thereof. Antibodies produced in the inoculated animal which specifically bind gamma interferon, TNF-alpha or IL-1 are then isolated from fluid obtained from the animal. Antibodies may be generated in this manner in several non-human mammals such as, but not limited to goat, sheep, horse, camel, rabbit, and donkey. Methods for generating polyclonal antibodies are well known in the art and are described, for example in Harlow, et al. (1988, In: Antibodies, A Laboratory Manual, Cold Spring Harbor, N.Y.).

When the antibody used in the methods of the invention is a monoclonal antibody, the antibody is generated using any well known monoclonal antibody preparation procedures such as those described, for example, in Harlow et al. (supra) and in Tuszynski et al. (1988, Blood, 72:109-115). Generally, monoclonal antibodies directed against a desired antigen are generated from mice immunized with the antigen using standard procedures as referenced herein. Monoclonal antibodies directed against full length or peptide fragments of gamma interferon, TNF-alpha or IL-1 may be prepared using the techniques described in Harlow, et al. (supra).

When the antibody used in the methods of the invention is a biologically active antibody fragment or a synthetic antibody corresponding to antibody to gamma interferon, an antibody to TNF-alpha or an antibody to IL-1, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology which is available in the art, and described, for example, in Wright et al. (1992, Critical Rev. in Immunol. 12(3,4):125-168) and the references cited therein. Alternatively, quantities of the desired antibody or fragment thereof may also be synthesized using chemical synthesis technology. If the amino acid sequence of the antibody is known, the desired antibody can be chemically synthesized using methods known in the art.

The present invention also includes the use of humanized antibodies specifically reactive with gamma interferon epitopes. The present invention further includes the use of humanized antibodies specifically reactive with TNF-alpha or IL-1 epitopes. These antibodies are capable of neutralizing human gamma interferon, human TNF-alpha or human IL-1. The humanized antibodies of the invention have a human framework and have one or more complementarity determining regions (CDRs) from an antibody, typically a mouse antibody, specifically reactive with gamma interferon, IL-1 or TNF-alpha. Thus, the humanized gamma interferon antibodies of the present invention are useful in the treatment of a herpes simplex virus infection, including an HSV-1 infection, such as a cold sore and an HSV-2 infection, such as genital herpes. The humanized gamma interferon antibodies of the present invention are useful in the treatment of other such diseases which are characterized by an autoimmune or inflammatory reaction which includes overproduction of gamma interferon, TNF-alpha and/or IL-1, such as seborrheic dermatitis.

When the antibody used in the invention is humanized, the antibody can be generated as described in Queen, et al. (U.S. Pat. No. 6,180,370), Wright et al., (supra) and in the references cited therein, or in Gu et al. (1997, Thrombosis and Hematocyst 77(4):755-759), or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as human gamma interferon, TNF-alpha or IL-1, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671. CDRs useful in producing the antibodies of the present invention may be similarly derived from DNA encoding monoclonal antibodies capable of binding to human IFN gamma, human TNF-alpha or human IL-1. Such humanized antibodies may be generated using well known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources such as the American Type Culture Collection, Manassas, Va.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies.

Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The use of Old World and New World camelids for the production of antibodies is contemplated in the present invention, as are other methods for the production of camelid antibodies set forth herein.

The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species. As an example, the production of antibodies in mammals is detailed in such references as Harlow et al., (1989, Antibodies: A Laboratory Manual, Cold Spring Harbor, N.Y.). Camelid species for the production of antibodies and sundry other uses are available from various sources, including but not limited to, Camello Fataga S. L. (Gran Canaria, Canary Islands) for Old World camelids, and High Acres Llamas (Fredricksburg, Tex.) for New World camelids.

The isolation of camelid antibodies from the serum of a camelid species can be performed by many methods well known in the art, including but not limited to ammonium sulfate precipitation, antigen affinity purification, Protein A and Protein G purification, and the like. As an example, a camelid species may be immunized to a desired antigen, for example gamma interferon, IL-1, or a TNF-alpha peptide, or fragment thereof, using techniques well known in the art. The whole blood can them be drawn from the camelid and sera can be separated using standard techniques. The sera can then be absorbed onto a Protein G-Sepharose column (Pharmacia, Piscataway, N.J.) and washed with appropriate buffers, for example 20 mM phosphate buffer (pH 7.0). The camelid antibody can then be eluted using a variety of techniques well known in the art, for example 0.15M NaCl, 0.58% acetic acid (pH 3.5). The efficiency of the elution and purification of the camelid antibody can be determined by various methods, including SDS-PAGE, Bradford Assays, and the like. The fraction that is not absorbed can be bound to a Protein A-Sepharose column (Pharmacia, Piscataway, N.J.) and eluted using, for example, 0.15M NaCl, 0.58% acetic acid (pH 4.5). The skilled artisan will readily understand that the above methods for the isolation and purification of camelid antibodies are exemplary, and other methods for protein isolation are well known in the art and are encompassed in the present invention.

The present invention further contemplates the production of camelid antibodies expressed from nucleic acid. Such methods are well known in the art, and are detailed in, for example U.S. Pat. Nos. 5,800,988; 5,759,808; 5,840,526, and 6,015,695, which are incorporated herein by reference in their entirety. Briefly, cDNA can be synthesized from camelid spleen mRNA. Isolation of RNA can be performed using multiple methods and compositions, including TRIZOL (Gibco/BRL, La Jolla, Calif.) further, total RNA can be isolated from tissues using the guanidium isothiocyanate method detailed in, for example, Sambrook et al. (1989, Molecular Cloning, A Laboratory Manual, Cold Spring Harbor, N.Y.). Methods for purification of mRNA from total cellular or tissue RNA are well known in the art, and include, for example, oligo-T paramagnetic beads. cDNA synthesis can then be obtained from mRNA using mRNA template, an oligo dT primer and a reverse transcriptase enzyme, available commercially from a variety of sources, including Invitrogen (La Jolla, Calif.). Second strand cDNA can be obtained from mRNA using RNAse H and *E. coli* DNA polymerase I according to techniques well known in the art.

Identification of cDNA sequences of relevance can be performed by hybridization techniques well known by one of ordinary skill in the art, and include methods such as Southern blotting, RNA protection assays, and the like. Probes to identify variable heavy immunoglobulin chains ($V_{HH}$) are available commercially and are well known in the art, as detailed in, for example, Sastry et al., (1989, Proc. Nat'l. Acad. Sci. USA, 86:5728). Full-length clones can be produced from cDNA sequences using any techniques well known in the art and detailed in, for example, Sambrook et al. (1989, Molecular Cloning, A Laboratory Manual, Cold Spring Harbor, N.Y.).

The clones can be expressed in any type of expression vector known to the skilled artisan. Further, various expression systems can be used to express the $V_{HH}$ peptides of the present invention, and include, but are not limited to eukaryotic and prokaryotic systems, including bacterial cells, mammalian cells, insect cells, yeast cells, and the like. Such methods for the expression of a protein are well known in the art and are detailed elsewhere herein.

The $V_{HH}$ immunoglobulin proteins isolated from a camelid species or expressed from nucleic acids encoding such proteins can be used directly in the methods of the present invention, or can be further isolated and/or purified using methods disclosed elsewhere herein.

The present invention is not limited to $V_{HH}$ proteins isolated from camelid species, but also includes $V_{HH}$ proteins isolated from other sources such as animals with heavy chain disease (Seligmann et al., 1979, Immunological Rev. 48:145-167, incorporated herein by reference in its entirety). The present invention further comprises variable heavy chain immunoglobulins produced from mice and other mammals, as detailed in Ward et al. (1989, Nature 341:544-546, incorporated herein by reference in its entirety). Briefly, $V_H$ genes were isolated from mouse splenic preparations and expressed in *E. coli*. The present invention encompasses the use of such heavy chain immunoglobulins in the treatment of various autoimmune disorders detailed herein.

As used herein, the term "heavy chain antibody" or "heavy chain antibodies" comprises immunoglobulin molecules derived from camelid species, either by immunization with an peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used therapeutically.

In addition to the antibodies discussed above, other "substantially homologous" modifications to native gamma interferon, TNF-alpha or IL-1 antibody sequences can be readily designed and manufactured using various recombinant DNA techniques well known to those skilled in the art. Moreover, a variety of different human framework regions may be used singly or in combination as a basis for humanizing antibodies directed at gamma interferon, TNF-alpha and IL-1. In general, modifications of genes may be readily accomplished using a variety of well-known techniques, such as site-directed mutagenesis (Gillman and Smith, Gene, 8, 81-97 (1979); Roberts et al., 1987, Nature, 328, 731-734).

Substantially homologous sequences to a gamma interferon antibody sequence are those which exhibit at least about 85% homology, usually at least about 90%, and preferably at least about 95% homology with a reference gamma interferon immunoglobulin protein. Further, substantially homologous sequences to a TNF-alpha antibody sequence are those which exhibit at least about 85% homology, usually at least about 90%, and preferably at least about 95% homology with a reference TNF-alpha immunoglobulin protein. In addition, substantially homologous sequences to an IL-1 antibody sequence are those which exhibit at least about 85% homology, usually at least about 90%, and preferably at least about 95% homology with a reference IL-1 immunoglobulin protein.

Alternatively, polypeptide fragments comprising only a portion of the primary antibody structure may be produced, which fragments possess one or more functions of gamma interferon, TNF-alpha or IL-1 antibody. These polypeptide fragments may be generated by proteolytic cleavage of intact antibodies using methods well known in the art, or they may be generated by inserting stop codons at the desired locations in vectors comprising the fragment using site-directed mutagenesis.

DNA encoding an antibody to gamma interferon, TNF-alpha or IL-1 are expressed in a host cell driven by a suitable promoter regulatory sequence which is operably linked to the DNA encoding the antibody. Typically, DNA encoding the antibody is cloned into a suitable expression vector such that the sequence encoding the antibody is operably linked to the promoter/regulatory sequence. Such expression vectors are typically replication competent in a host organism either as an episome or as an integral part of the host chromosomal DNA. Commonly, an expression vector will comprise DNA encoding a detectable marker protein, e.g., a gene encoding resistance to tetracycline or neomycin, to permit detection of cells transformed with the desired DNA sequences (U.S. Pat. No. 4,704,362).

*Escherichia coli* is an example of a prokaryotic host which is particularly useful for expression of DNA sequences encoding the antibodies of the present invention. Other microbial hosts suitable for use include but are not limited to, *Bacillus subtilis*, and other enterobacteriaceae, such as selected member of *Salmonella*, *Serratia*, and various *Pseudomonas* species. It is possible to generate expression vectors suitable for the desired host cell wherein the vectors will typically comprise an expression control sequence which is compatible with the host cell. A variety of promoter/regulatory sequences are useful for expression of genes in these cells, including but not limited to the lactose promoter system, a tryptophan (trp) promoter system, a beta-lactamase promoter system, or a promoter system derived from phage lambda. The promoter will typically control expression of the antibody whose DNA sequence is operably linked thereto, the promoter is optionally linked with an operator sequence and generally comprises RNA polymerase and ribosome binding site sequences and the like for initiating and completing transcription and translation of the desired antibody.

Yeast is an example of a eukaryotic host useful for cloning DNA sequences encoding the antibodies of the present invention. *Saccharomyces* is a preferred eukaryotic host. Promoter/regulatory sequences which drive expression of nucleic acids in eukaryotic cells include but are not limited to the 3-phosphoglycerate kinase promoter/regulatory sequence and promoter/regulatory sequences which drive expression of nucleic acid encoding other glycolytic enzymes.

In addition to microorganisms, mammalian tissue cell culture may also be used to express and produce the antibodies of the present invention (Winnacker, 1987, "From Genes to Clones," VCH Publishers, New York, N.Y.). Eukaryotic cells are preferred for expression of antibodies and a number of suitable host cell lines have been developed in the art, including Chinese Hamster Ovary (CHO) cells, various COS cell lines, HeLa cells, preferably myeloma cell lines, and transformed B-cells or hybridomas. Expression vectors which express desired sequences in these cells can include expression control sequences, such as an origin of DNA replication, a promoter, an enhancer (Queen et al., 1986, Immunol. Rev., 89, 49-68), and necessary processing sequence sites, such as ribosome binding sites, RNA splice sites, polyadenylation sites, and transcriptional initiation and terminator sequences. Preferred expression control sequences are promoters derived from immunoglobulin genes, Simian Virus (SV) 40, adenovirus, cytomegalovirus, bovine papilloma virus and the like.

The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (Sambrook et al., 1989, Molecular Cloning, A Laboratory Manual, Cold Spring Harbor, N.Y.).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used therapeutically.

The antibodies of the invention may be used in a therapeutic setting in a pharmaceutical acceptable carrier either alone, or they may be used together with a chemotherapeutic agent such as a non-steroidal anti-inflammatory drug, a corticosteroid, or an immunosuppressant. In addition, the antibodies of the present invention can be combined with anti-viral pharmaceutical compositions, including, but not limited to Acyclovir, Famciclovir and Valacyclovir. The antibodies, or complexes derived therefrom, can be prepared in a pharmaceutically accepted dosage form which will vary depending on the mode of administration.

The invention thus embodies a composition comprising antibodies that bind with gamma interferon, TNF-alpha or IL-1, alone or in combination, for use in treatment of a herpes simplex virus infection. As stated above, the antibodies can be monoclonal antibodies, polyclonal antibodies, humanized monoclonal antibodies, or monoclonal chimeric antibodies, or a biologically active fragment of any type of antibody herein recited. Generation of each type of antibody is discussed herein and applies to generation of antibodies for use in the novel methods of the invention. Generally, it is preferred that monoclonal humanized antibodies are used because they are non-immunogenic, and thus, will not elicit an immune response. However, any type of antibody may be used in the present invention, including polyclonal antibodies as disclosed elsewhere herein.

The method of the invention is not intended to be limited to use of antibodies to gamma interferon, TNF-alpha or IL-1. Inhibitors to gamma interferon, inhibitors of TNF alpha and inhibitors of IL-1 are also useful in the method of the invention. Such inhibitors include, but are not limited to, peptides which block the function or production of gamma interferon, gamma interferon receptor, antibodies to gamma interferon receptors, antibodies to IFN beta, antibodies to IFN alpha, interleukin-10 (IL-10), removal of IL-6 via an anti-IL-6 antibody (1988, Matsuda et al., Eur. J. Immunol., 18: 951-956) peptides which block the function of TNF-alpha, TNF-alpha receptor, antibodies to TNF-alpha receptor, peptides which block the function of IL-1, receptors for IL-1, antibodies to IL-1 receptors, and any combination thereof. In addition, the present invention encompasses the removal or inhibition of nitric oxide or nitric oxide synthase. Such compounds that could be administered include, but are not limited to free radical scavengers, enzyme inhibitors that inhibit nitric oxide synthase, and an antibody to nitric oxide synthase (1992, Ohsima et al, Biochem. Biophys. Res. Commun. 187: 1291-1297). Nitric oxide inhibitors and nitric oxide synthase inhibitors can also be used to treat other different autoimmune diseases, other than atherosclerosis.

Particularly contemplated additional agents include IFN gamma receptor, TNF alpha receptor, antibodies to IFN gamma receptors, an antibody to a TNF alpha receptor, IFN beta, interleukin-10 (IL-10), and any combination thereof. IL-10 can be produced and administered according to those methods known in the art, including those set forth in U.S. Pat. Nos. 5,231,012 and 5,328,989. The isolation of human interferon gamma receptor is well known in the art, and is described in, for example, U.S. Pat. Nos. 5,578,707; 5,221,789; and 4,897,264. Recombinant production of a human interferon gamma receptor, and antibodies that specifically bind a human interferon gamma receptor are well known in the art as well, and is described in, for example, Fountoulakis et al. (1990, J. Biol. Chem. 265: 13268-13275). Also contemplated in the present invention are chimeric interferon gamma receptors, wherein the chimeric interferon gamma receptor comprises a human interferon gamma receptor fused to another protein, such as, but not limited to a human IgG fragment, or the Fc portion of a human immunoglobulin molecule (Fountoulakis et al., 1995, J. Biol. Chem. 270: 3958-3964; Mesa et al., 1995, J. Interferon Cytokine Res. 15: 309-315). Further, the skilled artisan, when equipped with the present disclosure and the methods detailed herein, will readily be able to generate monoclonal, polyclonal and heavy chain antibodies to human interferon gamma receptor, as well as biologically active fragments and the like.

In addition to the administration of an interferon gamma receptor and antibodies that specifically bind an interferon gamma receptor, the present invention encompasses the administration of soluble TNF-alpha receptors, and antibodies thereto. That is, the present invention provides methods for treating a herpes simplex virus infection by administering soluble receptors to TNF-alpha, as well as antibodies to TNF alpha receptors. A soluble TNF-alpha receptor is well known in the art, and isolation from humans is described in, for example, Schall et al. (1990, Cell 61: 361-370). Further, the production of a recombinant soluble TNF-alpha receptor is described in, for example, Gray et al. (1990, Proc. Nat'l. Acad. Sci. USA 87: 7380-7384). The invention further encompasses the administration of antibodies to a TNF-alpha receptor. Such antibodies are well known in the art, and the skilled artisan, when armed with the present invention and the disclosure set forth herein, will readily be able to produce such antibodies. Further, the production of antibodies to a TNF-alpha receptor is described in, for example, Engelmann et al. (J. Biol. Chem. 1990: 265: 14497-14504). Also included in the present invention are a chimeric TNF-alpha receptor, wherein the chimeric protein comprises the 75 kDa or 55 kDa TNF-alpha receptor fused to another protein, such as a human immunoglobulin molecule, or fragments thereof. Such chimeric TNF-alpha receptor fusion proteins are well known in the art, and are described in, for example, Peppel et al. (1991, J. Exp. Med. 174: 1483-1489) and are available commercially, for example, etanercept (Amgen, Inc. Thousand Oaks, Calif.).

The present invention further comprises a human IL-1 receptor and antibodies that specifically bind a human IL-1 receptor. Such antibodies and receptors are well known in the art, and are described in, for example, U.S. Pat. No. 4,968, 607. Further, the skilled artisan, when equipped with the present disclosure and the methods detailed herein, will readily be able to generate monoclonal, polyclonal and heavy chain antibodies to human IL-1 receptor, as well as biologically active fragments and the like.

The invention disclosed herein further comprises the administration of an inhibitor of CD20, a B-cell ligand. An inhibitor of CD20 can be, for example, an anti-CD20 antibody, such as rituximab (RITUXAN, Genentech, South San Francisco, Calif.). In addition, the present invention encompasses the administration of a CD4 inhibitor, such as an antibody to CD4. Such antibodies are well known in the art and can be produced using the methods disclosed herein for the production of antibodies. Alternatively, an anti-CD4 antibody can obtained from commercial sources (HU-MAX CD4, Genmab, Copenhagen, Denmark).

The pharmaceutical composition useful for practicing the invention may be administered to deliver a dose of between one microgram per kilogram per day and one hundred milligrams per kilogram per day.

Pharmaceutical compositions that are useful in the methods of the invention may be administered topically or systemically in injectable or other similar formulations. Such injectable formulations include formulations for transdermal, subcutaneous, intramuscular, intravenous, intradermal, cutaneously, and local administration. Topical administration as used herein further includes inhalation administration, administration of a spray comprising an antibody of the present invention, and other topical methods of administration known in the art. The present invention further encompasses pharmaceutical compositions for administration via inhalation. In addition to the antibodies to gamma interferon, IL-1 and TNF-alpha, alone or in combination, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the gamma interferon antibodies according to the methods of the invention.

Compounds comprising antibodies to gamma interferon, TNF-alpha or IL-1, alone or in combination, that can be pharmaceutically formulated and administered to an animal for treatment of a herpes simplex virus infection, are now described.

The invention encompasses the preparation and use of pharmaceutical compositions comprising antibodies to gamma interferon, antibodies to TNF-alpha or antibodies to IL-1, alone or in combination, as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein. Ionophoretic administration of the pharmaceutical composition of the invention is considered a form of topical administration herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parenterally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for topical administration. Such formulations may, for example, be in the form of liquid, ointment, salve, lotion, cream, and the like, including, for example, a 0.1% to 100% (w/w) solution or suspension of the active ingredient in an aqueous or oily liquid carrier. Such drops may further comprise buffering agents, salts, or one or more other of the additional ingredients described herein. Other administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Preferably, the composition of the invention is administered topically. The composition may be administered as an ointment or in liquid form to the skin on or near the affected area (e.g. the lips, genitals and mouth). Preferably, the composition is administered in the form of an application of an antibody to the affected skin. However, the composition comprising antibody to gamma interferon, TNF-alpha or IL-1, alone or in combination, may also be administered parenterally.

As an example, a topical formulation can contain conventional carriers. By way of non-limiting example, the ointments may contain water and one or more hydrophobic carriers selected from, for example, liquid paraffin, polyoxyethylene alkyl ether, propylene glycol and white vaseline. The carrier compositions of the creams are typically based on water and white vaseline, in combination with glycerol and more minor components, e.g. one or more of glycerinemonostearate, PEG-glycerinemonostearate and cetylstearyl alcohol. The gels may by way of example be formulated using isopropyl alcohol and water, suitably in combination with minor components, for example one or more of glycerol and hydroxyethyl cellulose.

In addition, a topical formulation can contain a carrier capable of crossing cellular membranes, such as DMSO in solution with an antibody of the present invention. Such solutions of DMSO can be from about 5% to about 100% DMSO, preferably about 15% to about 90% DMSO, even more preferably about 15% to about 70% DMSO. In addition, DMSO can be used alone, or in combination with an antibody to a cytokine, such as gamma interferon, TNF-alpha and IL-1, a retinoid and an antibiotic.

An ointment, salve, cream, lotion, gel, shampoo and the like, can further comprise a moisturizing agent. The moisturizing agent can be a hydrophobic moisturizing agent such as ceramide, borage oil, tocopherol, tocopherol linoleate, dimethicone, glycerine, or a mixture thereof or a hydrophilic moisturizing agent such as hyaluronic acid, sodium peroxylinecarbolic acid, wheat protein, hair keratin amino acids, or a mixture thereof. The pharmaceutical composition can further include a pharmaceutically acceptable carrier or excipient. The pharmaceutical composition can be a gel, paste, cream, lotion, emulsion, or ointment.

Suitable dosage forms for topical administration include, but are not limited to, dispersions, lotions; creams; gels; pastes; powders; aerosol sprays; syrups or ointments on sponges or cotton applicators; and solutions or suspensions in an aqueous liquid, non-aqueous liquid, oil-in-water emulsion, or water-in-oil liquid emulsion. Because of its ease of administration, a cream, lotion, or ointment represents the most advantageous topical dosage unit form, in which case liquid pharmaceutical carriers may be employed in the composition. These creams, lotions, or ointments, may be prepared as rinse-off or leave-on products, as well as two stage treatment products for use with other skin cleansing or managing compositions. The compositions can be administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the pharmaceutical composition of the invention.

The compositions of the invention may be prepared by any pharmaceutical methods, but all methods include the step of bringing into association the carrier(s) with the active ingredient, which constitutes one or more necessary ingredients. In general, the compositions are prepared by uniformly admixing the active ingredient with liquid carriers or finely divided solid carriers or both, and then, if necessary, shaping the product into the desired presentation.

The methods of the invention may further comprise administering one or more additional agents by a route of administration set forth herein. Any suitable route of administration may be employed for providing the patient with an effective dosage of the disclosed antibodies, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation and like forms of administration. Preferably, the composition is administered topically.

As an example, an antibody to gamma interferon, an antibody to TNF-alpha and an antibody to IL-1, alone or in combination, can be administered using direct injections to the skin area afflicted by a herpes simplex virus infection. Such injections can include cutaneous or subcutaneous injections using a syringe, such as a tuberculin syringe, directly in the affected area. One or more injections can be administered to the area surrounding the affected region.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, and other factors well known in the art.

The antibodies to gamma interferon, TNF-alpha, or IL-1, alone or in combination, may be present in a composition to be administered to the affected skin at a range of concentrations.

A composition comprising an antibody to gamma interferon can be administered to the affected skin several times per day, as disclosed elsewhere herein. Preferably, the composition is administered from one to about five times per day, and more preferably, the composition is administered from one to three times per day. Most preferred is administration of the composition every two hours for about one to about two minutes.

Gamma interferon antibodies, TNF alpha antibodies or IL-1 antibodies, alone or in combination, can be administered to the affected skin of a patient for as long as necessary to remedy a herpes simplex virus infection. Preferably, the patient receives treatment for about 2 to about 10 days. More preferably, the patient receives treatment for about 4 to about 7 days. The entire treatment of administering gamma interferon, TNF-alpha or IL-1 antibodies, alone or in combination, can be repeated.

The present invention further comprises the administration of additional compounds in order to treat a herpes simplex virus infection. An antibody to gamma interferon, TNF-alpha and an antibody to IL-1, alone or in combination can be administered in conjunction with a topical vitamin A derivative, otherwise known as a retinoid, such as adapalene, tazarotene, tretinoin and the like. Topical retinoids are available commercially, and include DIFFERIN (Galderma, Fort Worth Tex.), TAZORAC (Allergan, Irvine, Calif.), RETIN-A MICRO (OrthoNeutrogena, Raritan, N.J.), ACCUTANE (Roche Pharmaceuticals, Nutley, N.J.) and the like. The present invention further comprises the administration of vitamin D and its derivatives, such as cholecalciferol and the administration of zinc or a salt thereof.

The present invention further comprises the administration of a cytokine such that an antibody to the cytokine is developed in the patient. As an example, a cytokine, such as gamma interferon, TNF-alpha or IL-1 is administered to the patient, preferably in an inactive form, using techniques well known in the art. The patient then develops antibodies to gamma interferon, TNF-alpha or IL-1 and the disease is thereby treated. Such methods of vaccination or developing a vaccine against a cytokine are well known in the art and are disclosed in, for example, Zagury et al. (2001, Proc. Nat'l. Acad. Sci. USA 98: 8024-8029).

The present invention further includes kits for the treatment of a herpes simplex virus infection. The kits of the present invention comprise a compound, including an antibody to gamma interferon, an antibody to TNF-alpha and an antibody to IL-1, an applicator, and instructional materials which describe use of the compound to perform the methods of the invention. Although model kits are described below, the contents of other useful kits will be apparent to the skilled artisan in light of the present disclosure. Each of these kits is contemplated within the present invention. The kits of the present invention can further comprise an antibiotic and other pharmaceutical compositions for the treatment of a herpes simplex virus infection, either together or separately, along with an anti-cytokine antibody.

In one aspect, the invention includes a kit for treating a herpes simplex virus infection. The kit of the present invention can be used to treat herpes simplex virus type 1 and herpes simplex virus type 2. The kit is used in the same manner as the methods disclosed herein for the present invention. The kit can be used to administer an antibody to a patient with a herpes simplex virus infection. The kit comprises an antibody to gamma interferon, an antibody to TNF-alpha and an antibody to IL-1, alone or in combinations disclosed elsewhere herein. As a non-limiting example, the kit can comprise an antibody to gamma interferon. In another non-limiting example, the kit can comprise an antibody to TNF-alpha. In yet another example, the kit can comprise an antibody to IL-1. Other examples of kits contemplated in the present invention comprise an antibody to gamma interferon, and antibody to TNF-alpha, and an antibody to IL-1 in combinations disclosed elsewhere herein. Additionally, the kit comprises an applicator and an instructional material for the use of the kit. These instructions simply embody the examples provided herein.

The kit can further include a pharmaceutically-acceptable carrier. The antibody is provided in an appropriate amount as set forth elsewhere herein. Further, the route of administration and the frequency of administration are as previously set forth elsewhere herein.

As evidenced by the Examples disclosed herein, the present invention is particularly useful in treating a herpes simplex virus infection in a human patient Definitions The articles "a" and "an" are used herein to refer to one or to more than one (i.e. to at least one) of the grammatical object of the article. By way of example, "an element" means one element or more than one element.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "applicator" as the term is used herein, is meant any device including, but not limited to, a hypodermic syringe, a pipette, a foam or gauze pad, and the like, for administering an antibody to a human.

By the term "biologically active antibody fragment" is meant a fragment of an antibody which retains the ability to specifically bind to gamma interferon, TNF alpha or IL-1.

The term "interleukin-1" as used herein refers to both interleukin-1-alpha (IL-1α) and interleukin-1-beta (IL-1β), unless specified otherwise.

A "disease" is a state of health of an animal wherein the animal cannot maintain homeostasis, and wherein if the disease is not ameliorated then the animal's health continues to deteriorate. Use of the term disease throughout the application is meant to encompass the terms diseases, disorders, and conditions.

A "herpes simplex virus infection" as used herein refers to a manifestation of a detectable pathological event due to the presence of a herpes simplex virus, including herpes simplex virus 1 and/or herpes simplex virus 2, in a mammal.

"Treatment" of a disease occurs when the severity of a symptom of the disease, the frequency with which such a symptom is experienced by a patient, or both, is reduced or eliminated. For example, treatment of a herpes simplex virus infection, including herpes simplex type 1 and herpes simplex type 2, includes use of a composition comprising antibodies to gamma interferon, TNF-alpha or IL-1 after a herpes cold sore has already occurred.

By the term "specifically binds," as used herein, is meant an antibody which recognizes and binds gamma interferon, TNF-alpha or IL-1, but does not substantially recognize or bind other molecules in a sample.

"Autoimmune response" refers to an alteration in the immune system wherein the immune response mounted during a disease state is detrimental to the host. Typically, cells of the immune system or other immune system components such as antibodies produced by the host, recognize "self" antigens as foreign antigens.

A "hyperimmune response" refers to an autoimmune response characterized by an overexpression of one or more cytokines of the immune system.

A pharmaceutical composition is said to be "topically administered" when it is applied directly to the affected area of the skin. Gauze compresses, salves, liquids, lotions, topical sprays and adhesive patches, for example, are applied topically, as are creams and ointments. Ionophoresis is also included as a form of topical administration.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

"Recombinant DNA" refers to a polynucleotide having sequences that are not naturally joined together. An amplified or assembled recombinant polynucleotide may be included in a suitable vector, and the vector can be used to transform a suitable host cell. A recombinant DNA polynucleotide may serve a non-coding function (e.g., promoter, origin of replication, ribosome-binding site, etc.) as well.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Preparation of Antibodies

Anti-IFN-gamma antibodies were produced by immunizing goats with recombinant human IFN-gamma (Peprotech, Rocky Hill, N.J.) using methods well known in the art. Goats were plasmapheresed and the IgG was isolated. F(ab')$_2$ fragments were prepared by pepsin digestion and purified by gel filtration. Protein concentration was 33 mg/ml with an IFN-gamma neutralizing activity of >66 μg/ml as determined by a cell growth inhibition assay. F(ab')$_2$ fragments were suspended in phosphate buffered saline (PBS).

Example 2

Treatment of Herpes Cold Sores (Herpes Simplex Virus 1)

Patient 1, a 58 year old male with chronic recurring herpes simplex cold sores on the mouth presented with erythema and blisters. A gauze compress comprising anti-gamma interferon F(ab')$_2$ fragments was applied with mild pressure to the afflicted areas for one to two minutes, every two hours. After about 3 to about 3.5 hours, the patient noted a decrease in the burning and pain in the area of the lesions. The patient was administered antibodies to gamma interferon for an additional 2 days. After the additional two days of treatment, scabs formed which faded away in five days.

Patient 2, a 22 year old male with chronic recurring herpes simplex cold sores presented with blisters around the mouth. A gauze compress comprising anti-gamma interferon $F(ab')_2$ fragments was applied with mild pressure to the afflicted areas for one to two minutes, every two hours for one day. The patient noted that the period of burning and pain subsided more quickly than in the past and that scabs formed and disappeared more quickly than in previous herpes cold sore outbreaks.

Example 3

Treatment of Genital Herpes (Herpes Simplex 2)

Patient 3, a 28 year old female presented with genital herpes with a duration of two years with recurrences 1-2 times per month for 7-10 days per recurrence. Patient 3 described the lesions as itching and painful and skin erosion had occurred. Patient 3 was administered antibodies to gamma interferon via a gauze pad four times a day for two days. Patient 3 reported that within six hours of initial treatment, the itching and pain had subsided completely and three days after the initial treatment, the skin erosions epithelialized.

Patient 4, a 33 year old female, presented with genital herpes with duration of more than three years with recurrences 1-2 times per month accompanied by pain and burning sensations. At the time of presentation, 3-4 blisters were visible on the patient's genitalia. Approximately 50 minutes after treatment with antibodies to gamma interferon via topical administration (gauze pad), Patient 4 stated that the pain had completely subsided. Three hours after the initial treatment, slight itching persisted, which ceased after a second topical application of antibodies to gamma interferon. During the first day of treatment, Patient 4 subjectively noted periodic sensations of pain that subsided after additional application of antibodies to gamma interferon. On day two, the number of blisters increased to nine, but all subjective sensations of burning or pain were absent. On day four, skin erosions epithelialized and on day 5 all pathological and clinical indicators of genital herpes completely subsided.

Patient 5, a 38 year old male and Patient 4's husband, presented approximately two years after contracting genital herpes with recurrence one to two times every three months. Itching and pain accompanied the appearance of blisters. Treatment with antibodies to gamma interferon began when blisters first appeared with applications three times on day 1 and four times on day 2. Patient 5 reported no feelings of discomfort by day 2 and epithelialization of skin erosion occurred by the fourth day after treatment commenced.

Example 4

Treatment of Seborrheic Dermatitis

Patient PM, a 42 year old male, presented with erythema on the face, particularly the skin of the forehead at the hairline. The skin was peeling in large layers and described as itching. Antibodies to gamma interferon were applied three times a day for three days. Patient PM described the itching as decreasing on day two and the large peeling area became a smaller area characterized by scaling. By day three, the skin had become pale.

The results of the experiments disclosed establish that treatment of herpes simplex virus infections with antibody to gamma interferon is effective.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a herpes simplex virus infection in a patient, the method comprising administering to the patient an effective amount of an antibody to gamma interferon.

2. The method of claim 1, wherein the antibody is selected from the group consisting of a polyclonal antibody, a monoclonal antibody, a humanized antibody, a synthetic antibody, a heavy chain antibody, a biologically active fragment of an antibody, wherein the biologically active fragment is a Fab fragment, a F(ab')$_2$ fragment, a Fv fragment, and combinations thereof.

3. The method of claim 1, wherein the antibody is administered by the route selected from the group consisting of intramuscularly, intravenously, intradermally, cutaneously, ionophoretically, topically, locally, and inhalation.

4. The method of claim 3, wherein the antibody is administered topically.

5. The method of claim 4, wherein the antibody is selected from the group consisting of a polyclonal antibody, a monoclonal antibody, a synthetic antibody, a heavy chain antibody, a humanized antibody, a biologically active fragment of an antibody, wherein the biologically active fragment is a Fab fragment, a F(ab')$_2$ fragment, a Fv fragment, and combinations thereof.

6. The method of claim 5, wherein the heavy chain antibody is selected from the group consisting of a camelid antibody, a heavy chain disease antibody, and a variable heavy chain immunoglobulin.

7. The method of claim 1, wherein the herpes simplex virus infection is a herpes simplex type 1 infection.

8. The method of claim 1, wherein the herpes simplex virus infection is a herpes simplex type 2 infection.

* * * * *